United States Patent [19]
Landis

[11] Patent Number: 5,691,514
[45] Date of Patent: Nov. 25, 1997

[54] REARWARD SOUND ENHANCING APPARATUS

[75] Inventor: Timothy J. Landis, Loomis, Calif.

[73] Assignee: OP-D-OP, Inc., Roseville, Calif.

[21] Appl. No.: 586,086

[22] Filed: Jan. 16, 1996

[51] Int. Cl.⁶ .................. H04R 25/00; A42B 1/08
[52] U.S. Cl. .................. 181/129; 181/130; 381/187; 2/423; 2/425
[58] Field of Search .................. 181/129, 130, 181/135, 137; 381/183, 187, 169, 188; 2/422, 423, 425, 209

[56] References Cited

U.S. PATENT DOCUMENTS

| 373,835 | 5/1887 | Pitre. | |
|---|---|---|---|
| 4,471,174 | 9/1984 | Nava | 381/183 |
| 5,044,014 | 9/1991 | Cornale et al. | |
| 5,086,789 | 2/1992 | Tichy. | |
| 5,125,032 | 6/1992 | Meister et al. | 381/183 |
| 5,231,704 | 8/1993 | Hildenbrand. | |
| 5,361,419 | 11/1994 | Bernstein | 2/209 X |
| 5,438,702 | 8/1995 | Jackson | 2/425 |

FOREIGN PATENT DOCUMENTS

| 912921 | 6/1954 | Germany. |
|---|---|---|
| 479645 | 4/1953 | Italy. |
| 356552 | 9/1931 | United Kingdom. |

Primary Examiner—Khanh Dang
Attorney, Agent, or Firm—John P. O'Banion

[57] ABSTRACT

A head-worn acoustic receiver apparatus for use by cyclists and the like wherein an acoustic receiver cup is coupled to a cyclist helmet in a rearward facing direction. A microphone within the acoustic receiver cup receives sound reflected by the cup and directs the sound to earphones wherein the sound is reproduced and amplified for the wearer of the invention. Ear housings, which contain the earphones, are positioned over the wearer's ears to reduce the ambient wind noise associated with cycle travel.

9 Claims, 6 Drawing Sheets

FIG.—4

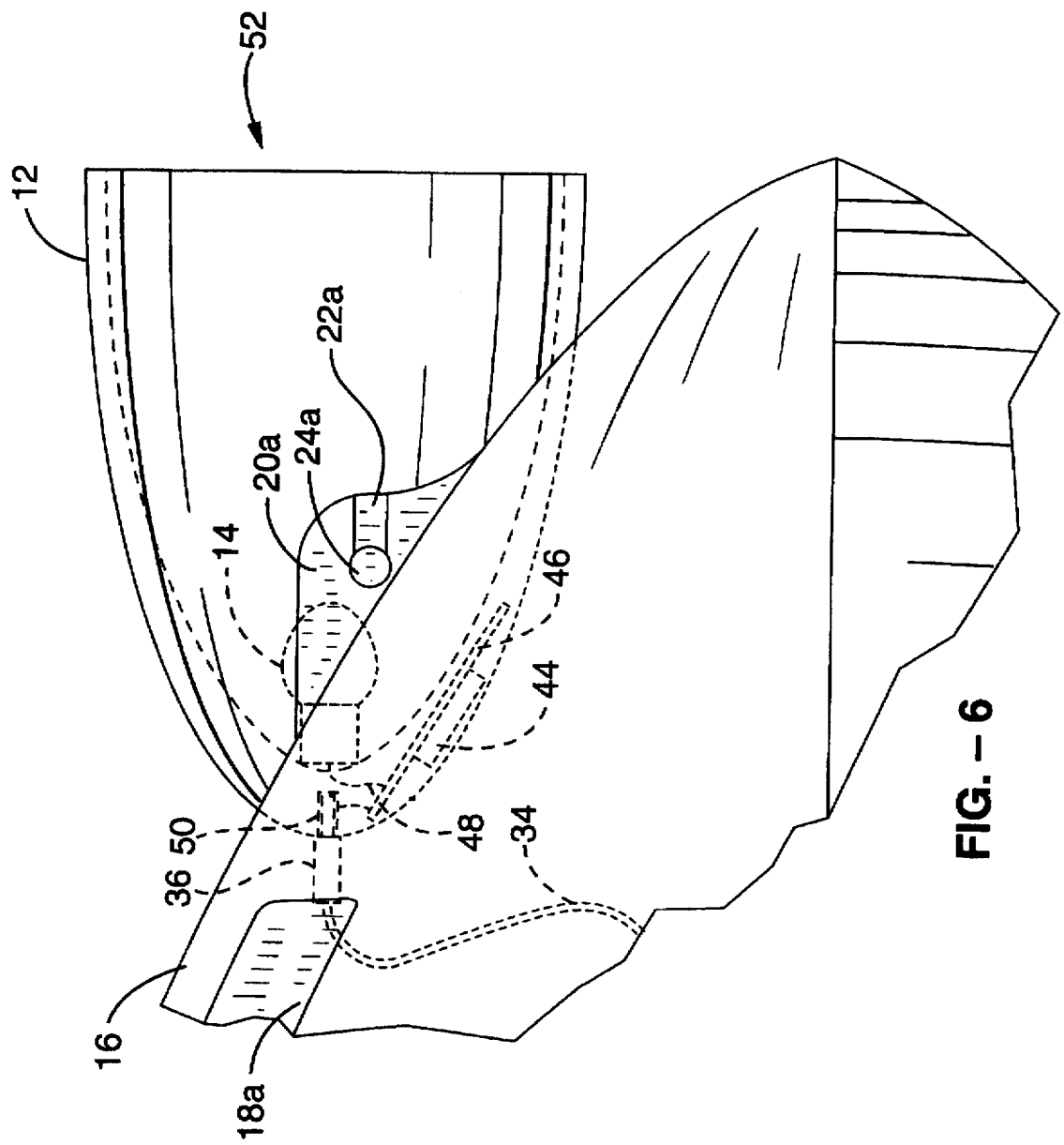

REARWARD SOUND ENHANCING APPARATUS

BACKGROUND OF THE INVENTION

1. Field of the Invention

This invention pertains generally to devices and methods for directional receiving and amplification of sound, and more particularly to a head-worn, rearward sound enhancing apparatus for use by cyclists and the like which amplifies sounds from behind the wearer and directs the amplified sounds to the wearer's ears.

2. Description of the Background Art

Bicycle travel has grown in popularity in recent years, and the number of bicycles and bicyclists has proliferated as people have generally become more health and environmentally conscious. One problem associated with bicycle travel is that the hearing of cyclists, especially in the rearward direction, is reduced by the noise caused by air or wind rushing past the ears due to the speed of travel. The reduced hearing associated with bicycle travel increases the risk of collisions with motor vehicles or other bicycles, particularly those approaching from the rear, because cyclists may not hear an approaching vehicle which they could otherwise react to in order to avoid a collision.

A variety of ear covering, ear protector, and wind-deflector devices have been developed to both protect the ears of cyclists and to reduce the wind noise associated with bicycle travel. Most of these devices comprise shell-like coverings which are held over the ears of a wearer by a resilient band or head encircling strap. Some of the known ear covering devices include rearwardly disposed openings which provide for passive sound amplification or collection from the rear. However, none of the previously disclosed ear covering and ear protecting devices provide adequate active rearward sound amplification which overcomes the wind noise associated with cycle travel sufficiently to allow cyclists to hear motor vehicles or other cyclists approaching from the rear.

Accordingly, there is a need for an apparatus which provides for the receiving and amplification of sounds from behind a wearer, which directs the amplified sound to a wearer's ears, which overcomes the wind noise associated with bicycle travel, and which increases the safety of bicycle travel. The present invention satisfies these needs, as well as others, and generally overcomes the deficiencies found in conventional devices.

SUMMARY OF THE INVENTION

The present invention pertains to a head-worn, rearward-facing, acoustic receiver apparatus for enhancing the hearing of cyclists in the rearward direction. In general terms, the invention comprises an acoustic receiver for picking up sound, a microphone associated with the acoustic receiver, ear housings or covers, and speakers associated with the ear housings, with the speakers being interfaced with the microphone. The invention also preferably includes a power supply for the microphone and speakers, first support means for supporting the acoustic receiver on a wearer's head or to a helmet, and second support means for positioning and holding the ear housings and speakers adjacent to a person's ears.

By way of example and not of limitation, the acoustic receiver comprises a generally parabolic-shaped sound-gathering receiver cup or dish which is positioned in a rearwardly disposed orientation relative to the head of a wearer. The microphone is preferably located at the nadir or central low point of the parabolic cup. The ear housings preferably comprise aerodynamically shaped coverings or cups, with speakers contained therewithin, and include rearward facing openings. The speakers preferably comprise conventional earphones or small audio speakers which are interfaced with the microphone and power supply by standard wiring. The positioning and holding means for the ear housings preferably comprises a resilient band worn vertically about a person's head, with the ear housings included at first and second ends of the resilient band. A helmet preferably serves as the means for supporting the acoustic receiver on a person's head, with the helmet having reversible attachment means for holding the acoustic receiver in a rearwardly disposed direction. The support means may alternatively comprise a headband or hat. The power supply preferably comprises a battery or batteries or a solar cell arrangement associated with the helmet.

The present invention is employed by affixing or attaching the acoustic receiver cup onto the rear of a helmet, and connecting the associated wiring between the microphone, power supply and speakers. Then, the user places the resilient band around his or her head and positions the ear housings over the ears, and puts on the cyclist helmet in a conventional manner. Sound received by the rearwardly oriented acoustic receiver cup is picked up by the microphone therein, amplified if necessary, and transmitted to the speakers within the ear coverings, allowing the user of the invention, while bicycling, to hear sounds from behind without the interference of wind noise due to bicycle travel. The acoustic receiver cup preferably is detachable from the cyclist helmet so that it can utilized with a different helmet or coupled directly to a person's head by a headband or like means.

An object of the invention is to provide an acoustic receiver apparatus which allows cyclists to hear the sounds of approaching traffic from behind.

Another object of the invention is to provide an acoustic receiver apparatus which eliminates the wind noise associated with bicycle travel.

Another object of the invention is to provide an acoustic receiver apparatus which may be interchangeably used with different cycling helmets.

Another object of the invention is to provide an acoustic receiver apparatus which is inexpensive.

Another object of the invention is to provide an acoustic receiver apparatus which is easy to use.

Another object of the invention is to provide an acoustic receiver apparatus which increases or enhances the safety of bicycle travel and reduces the risk of collision or accidents.

Further objects of the invention will be brought out in the following portions of the specification, wherein the detailed description is for the purpose of fully disclosing the invention without placing limits thereon.

BRIEF DESCRIPTION OF THE DRAWINGS

The invention will be more fully understood by reference to the following drawings which are for illustrative purposes only:

FIG. 6 is an enlarged fragment view of FIG. 4, showing the acoustic receiver cup, microphone and power supply in detail.

DESCRIPTION OF THE PREFERRED EMBODIMENTS

Referring more specifically to the drawings, for illustrative purposes the present invention is embodied in the apparatus which is generally shown in FIG. 1 through FIG. 6. It will be appreciated that the apparatus may vary as to configuration and as to details without departing from the basic concepts as disclosed herein.

Figure 1:
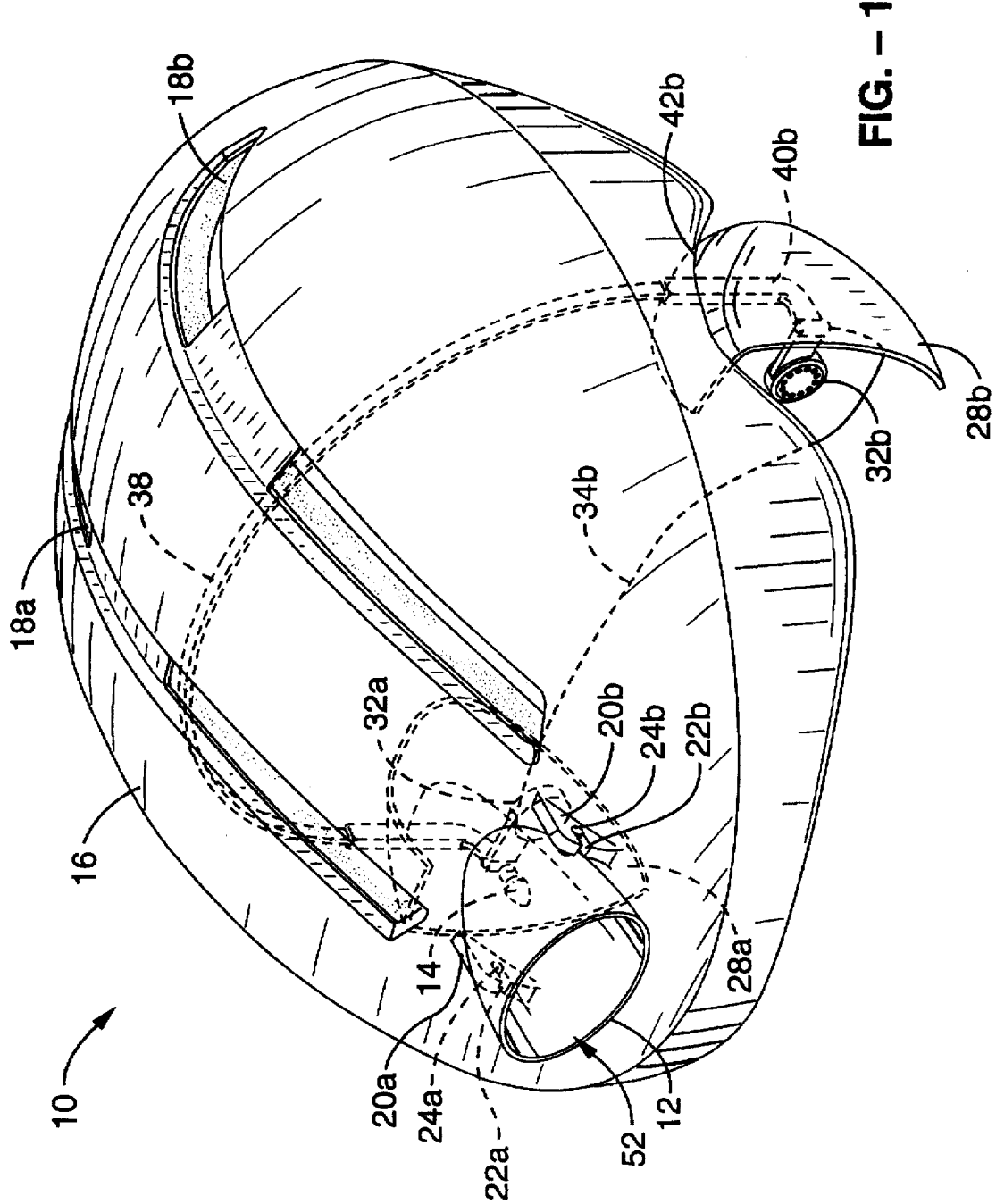
FIG. 1 is a perspective view of an apparatus in accordance with the present invention.
Figure 2:
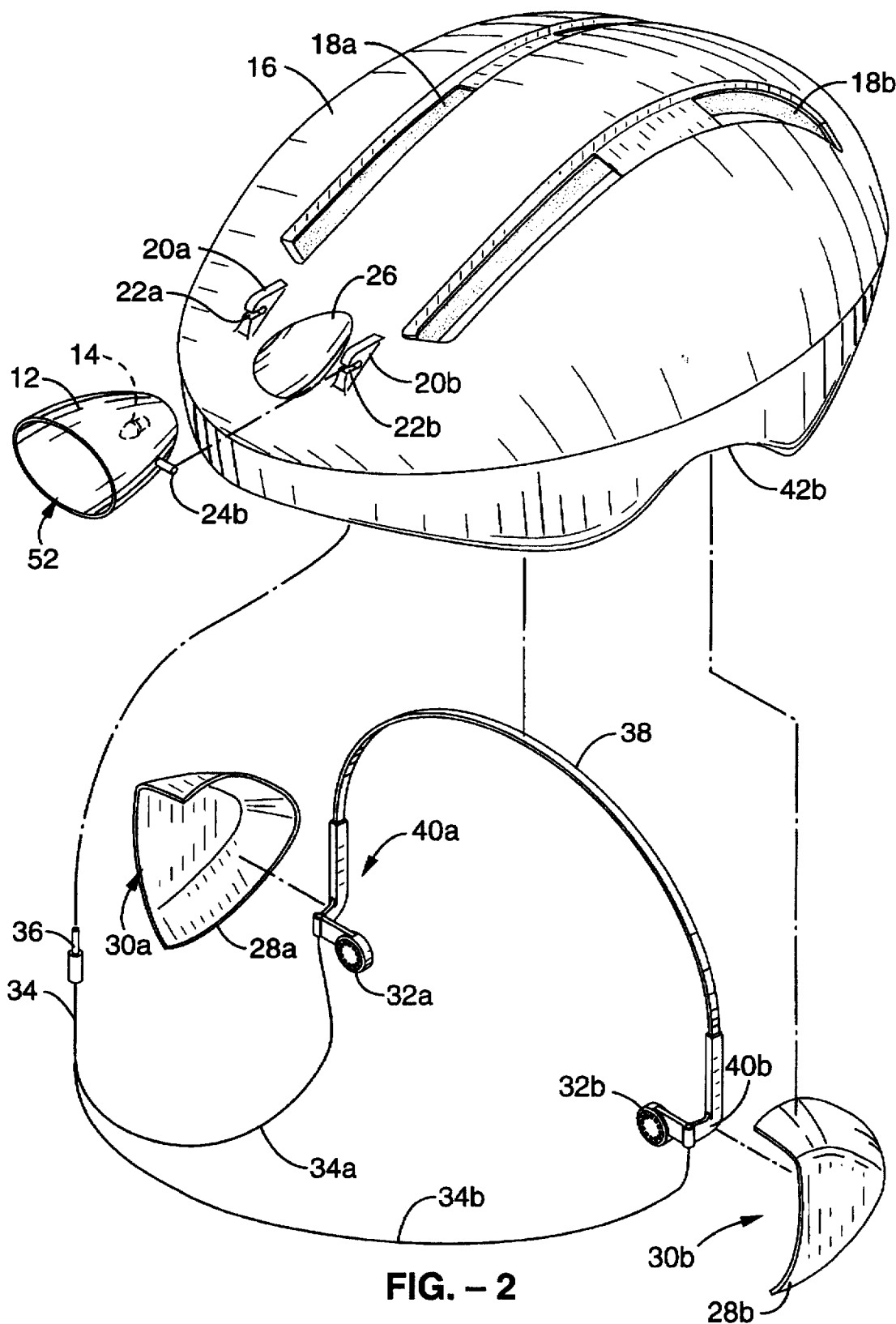
FIG. 2 is an exploded view of the apparatus shown in FIG. 1.

Referring first to FIG. 1 and FIG. 2, there is shown generally a rearward sound enhancing apparatus 10 in accordance with the present invention. The invention includes an acoustic receiver 12 for receiving or picking up sound, preferably in the form of a parabolic-shaped cup. Acoustic receiver 12 is worn or coupled to a wearer's head, as discussed further below, preferably in a rearward facing direction, to receive and provide amplification of sounds from behind the wearer. Acoustic receiver 12 may be of broad, shallow-angled configuration for receiving sounds over a relatively wide range of direction, or may be relatively narrow and steep angled for selectively receiving sound from a narrow range of direction, depending upon the particular application of the invention. A microphone 14 is provided within the interior of acoustic receiver 12, and is preferably positioned at the central low point or nadir of parabolic-shaped interior of acoustic receiver 12 for pick-up of acoustic waves reflected thereto by acoustic receiver 12. The acoustic receiver may alternatively comprise a plurality of cups arranged in a rearward facing array, with a microphone included in each of the cups.

Acoustic receiver 12 is preferably supported on a wearer's head by a conventional cycling helmet 16 or the like to which acoustic receiver 12 is coupled. A typical helmet 16 generally includes a shock-absorbing foamed core or interior (not shown) and a hard, impact resistant external shell (not shown) as is standard in the art. A pair of longitudinal openings 18a, 18b provide ventilation to the wearer's head (not shown) to increase comfort. A chin strap (not shown) may be provided for fastening helmet to a wearer's head. Conventional attachment means are used for coupling acoustic receiver 12 to helmet 16. As shown, the attachment means comprises a pair of mounting elements 20a, 20b attached to the rear portion of helmet 16, and preferably held thereto by adhesive, VELCRO® fasteners or other conventional means. Mounting elements 20a, 20b may alternatively be integral portions of helmet 16 and molded from the material comprising the exterior shell of helmet 16, or may be detachable for interchanging with different cycling helmets. Acoustic receiver 12, which is also preferably interchangeable with different helmets, is coupled to mounting elements 20a, 20b by a snap fitting arrangement or other conventional detachable coupling means. Mounting elements 20a, 20b are shown with slots 22a, 22b respectively which reversibly engage pins or keys 24a, 24b on acoustic receiver 12 by snap fitting. Alternative snap fitting arrangements or other attachment means may also be utilized with mounting elements 20a, 20b and acoustic receiver 12. A recessed portion 26 may be included on helmet 16 to accommodate acoustic receiver 12 if desired. Mounting elements 20a, 20b could alternatively be structured and configured to hold acoustic receiver 12 above the surface of helmet 16. It is also contemplated that acoustic receiver 12 could be an integral part of helmet 16, or otherwise be permanently attached to helmet 16.

The means for supporting or coupling acoustic receiver 12 to a wearer's head may alternatively comprise a head encircling strap or band instead of helmet 16, with acoustic receiver 12 fastened to the back of the strap in a rearward facing orientation. The coupling means could also comprise a hat or visor to which acoustic receiver 12 is attached by VELCRO® fasteners, buttons, or like fastening means. It is further contemplated that acoustic receiver 12 may be coupled to a wearers' head by means of a strap or band associated with goggles or eyeglasses.

Ear covers, shown as first and second ear housings 28a, 28b, are provided with the invention to eliminate the wind noise inherent in bicycle travel by preventing wind from rushing by the ears of a person wearing the invention. Ear housings 28a, 28b each include a rearward facing opening 30a, 30b, which provides air cooling to the wearer's ears as well as provide some passive hearing enhancement from the rearward direction. Preferably, ear housings 28a, 28b are fabricated from a compressed foam rubber material. Ear housings 28a, 28b may also include thermal and/or acoustic insulation (not shown) to protect ears from cold weather and further reduce wind noise if desired. Preferably, the exteriors of ear housings 28a, 28b are aerodynamically shaped to minimize wind noise. Ear housings 28a, 28b are preferably structured and configured to be worn together with cycling helmet 16, as discussed further below.

Figure 3:
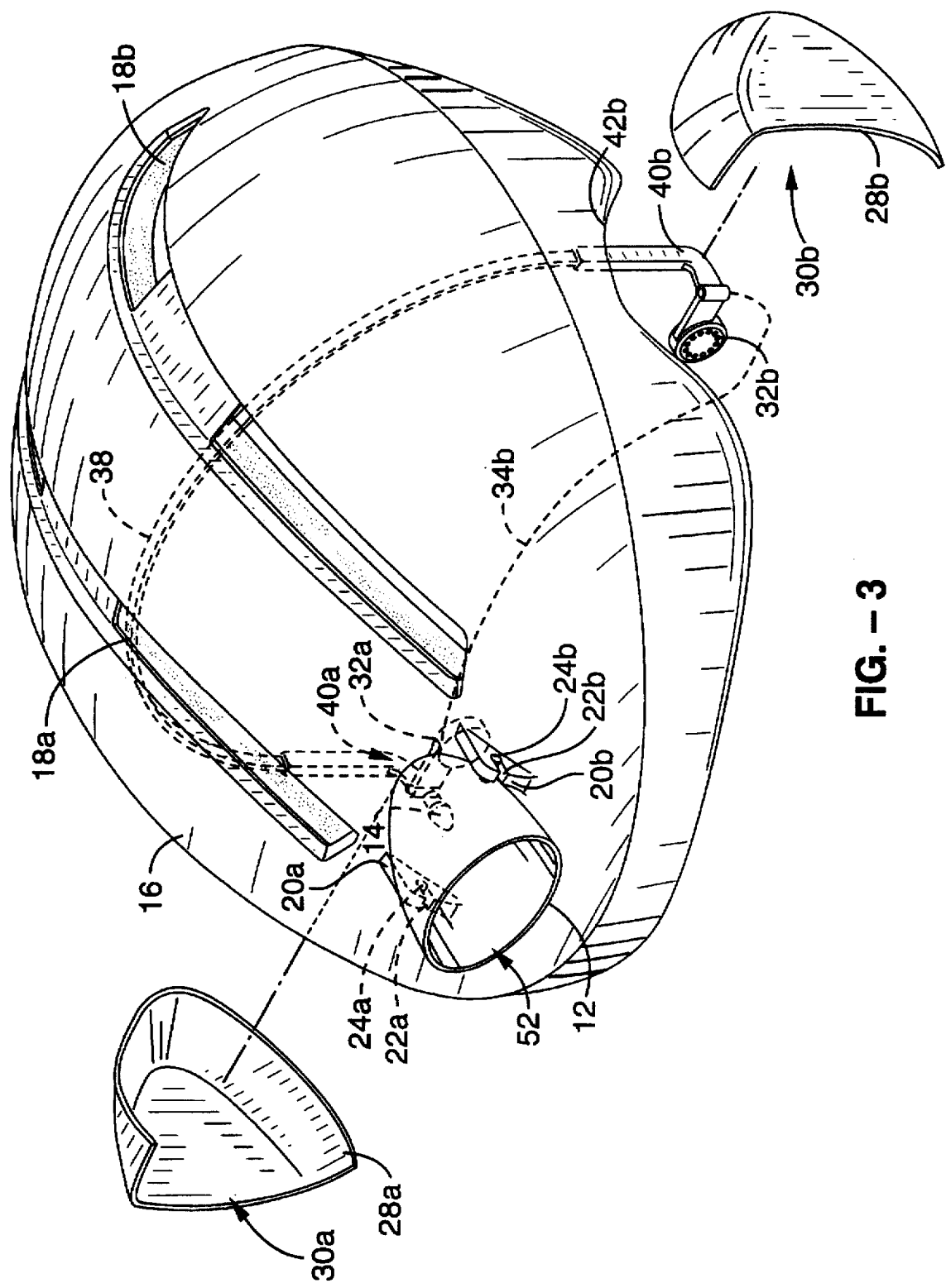
FIG. 3 (is a perspective view of the apparatus shown in FIG. 1 with the ear covers removed.
Figure 4:
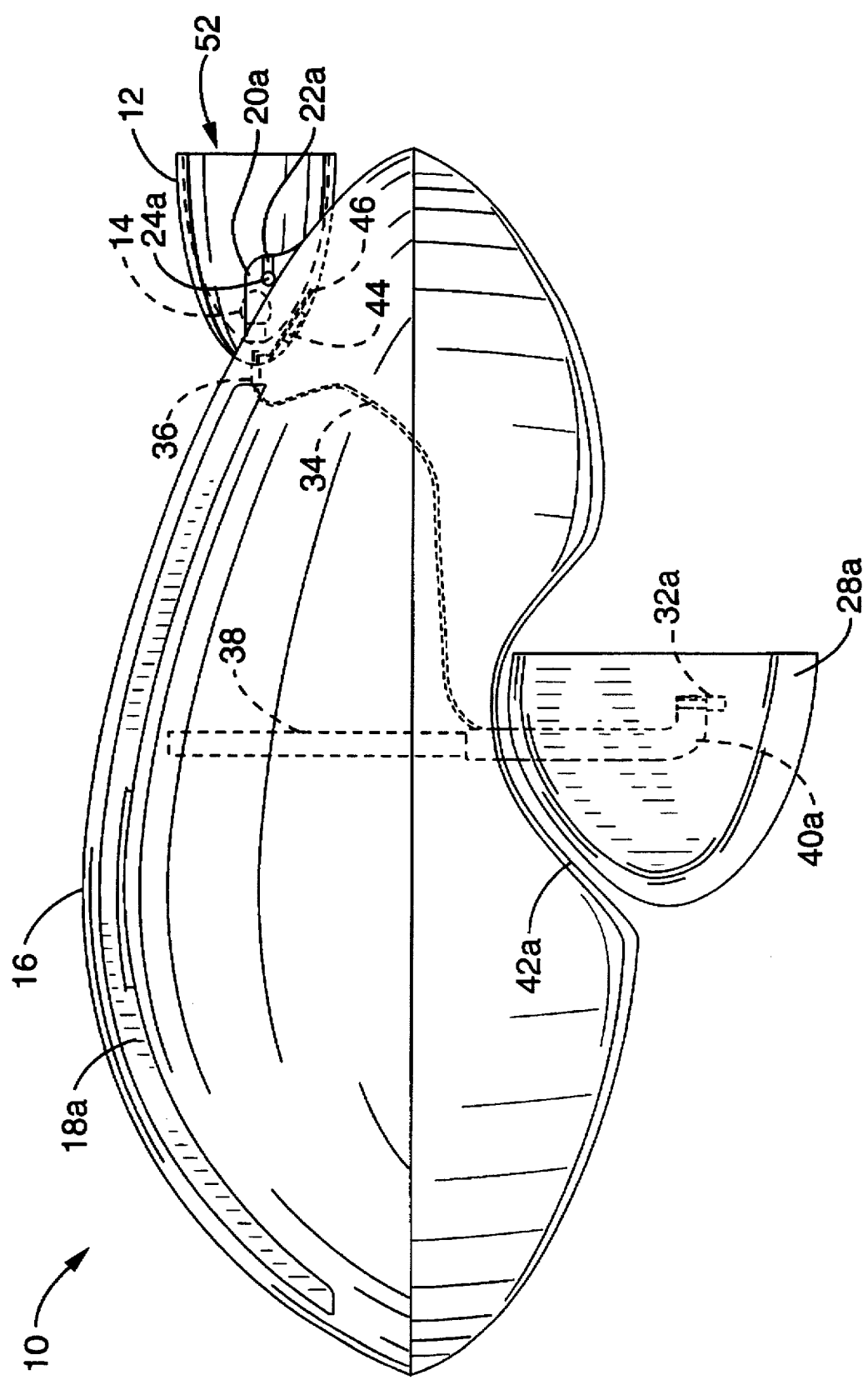
FIG. 4 is a rear view of the apparatus shown in FIG. 1.
Figure 5:
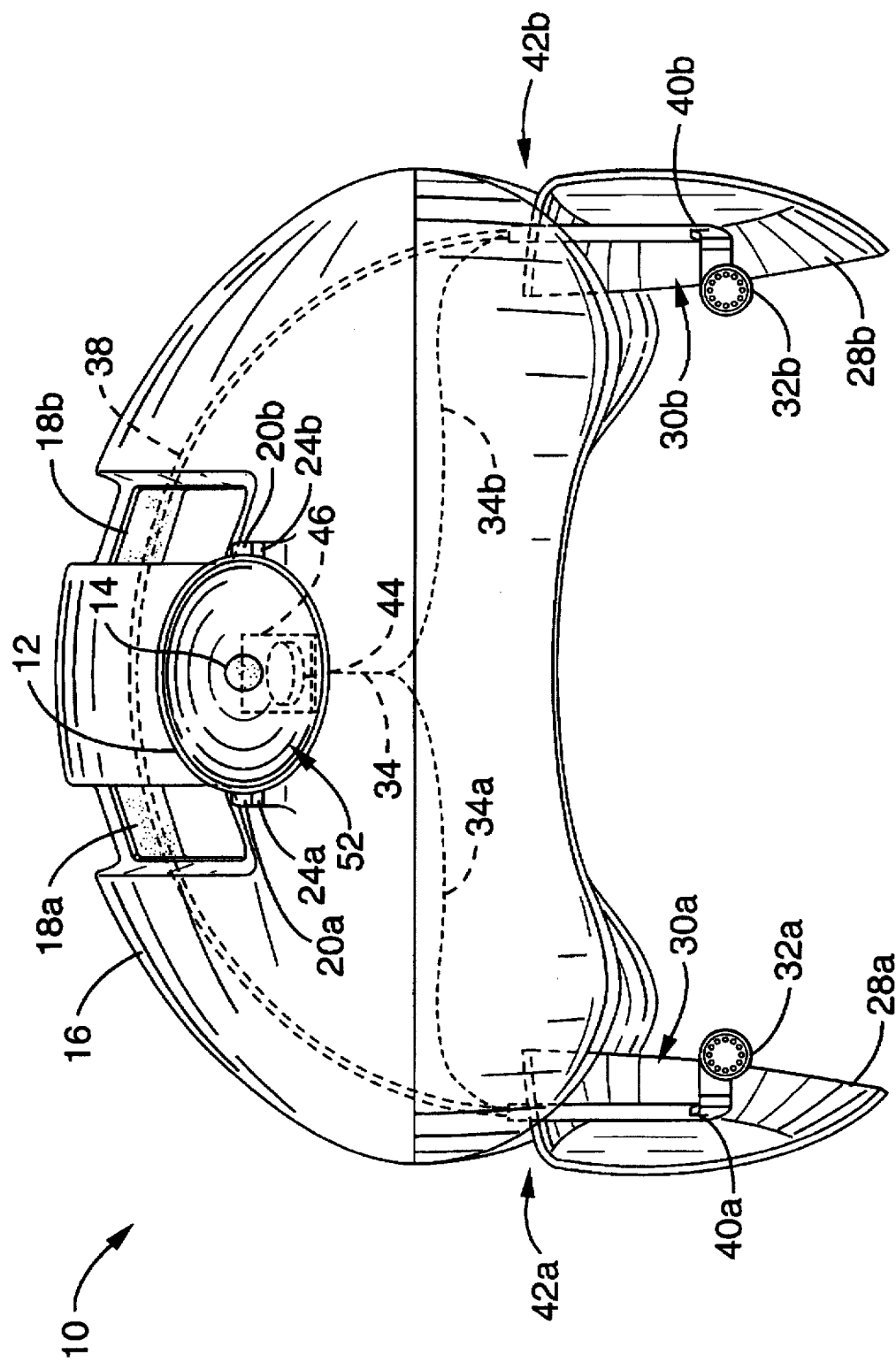
FIG. 5 is a side view of the acoustic receiver apparatus shown in FIG. 1.

Referring also to FIG. 3 through FIG. 5, first and second ear housings 28a, 28b, include a first earphone 32a and a second earphone 32b, respectively, which are positioned within the interiors of first and second ear housings 28a, 28b. First and second earphones 32a, 32b preferably comprise conventional audio speakers which are commonly utilized in stereo head sets such as SONY WALKMAN® head sets and the like. Earphones 32a, 32b are positioned within ear housings 28a, 28b so that earphones 32a, 32b will be adjacent to a wearer's ears. Earphones 32a, 32b are interfaced with microphone 14 via a conventional wiring bundle 34 which is bifurcated into branches 34a, 34b, with branches 34a, 34b connected to earphones 32a, 32b respectively. Wiring 34 may be internal to helmet 16, may be worn inside helmet 16 against a wearer's head, or may be worn outside of helmet 16. A jack 36 is provided with wiring 34 for connection with microphone 14, as discussed further below. It will also be appreciated that conventional amplifying circuitry could also be interposed between microphone 14 and earphones 32a, 32b in the event that the output of microphone 14 is insufficient to directly drive earphones 32a, 32b.

The invention includes support means for positioning and holding the ear housings 28a, 28b and earphones 32a, 32b adjacent to a wearer's ears, preferably in the form of a conventional hoop shaped head band 38 with first and second ends 40a, 40b. Generally, first earphone 32a and first ear housing 28a are affixed adjacent to first end 40a of headband 38, and second earphone 32b and second ear housing 28b are affixed adjacent to second end 40b of headband 38. Headband 38 preferably is worn with helmet 16 in a manner such that ear housings 32a, 32b are positioned adjacent notches 42a, 42b in helmet 16 and with headband 38 positioned within helmet 16 in a manner which is comfortable to a wearer. Headband 38 may be coupled to helmet 16 along the inside of helmet 16 by conventional means (not shown) such as VELCRO® fasteners or snap fitting. Ear housings 28a, 28b may alternatively be detachably coupled directly to helmet 16 by VELCRO® fasteners, snap fitting fasteners, or other standard coupling means, thus eliminating the need for head band 38. It is also contemplated that ear housings 28a, 28b could be integral portions of helmet 16, with the shell of helmet 16 and ear housings 28a, 28b fabricated from the same piece of material.

The invention may be used without ear housings 28a, 28b, with ear phones 32a, 32b positioned and held adjacent a wearer's ears by headband 38 as described above, with ear housings 28a, 28b removed from the ends 40a, 40b of head band 38. However, the wind noise generated by bicycle travel will reduce hearing of sounds from earphones 32a, 32b by persons using the invention, and thus ear coverings 28a, 28b are preferably used with the invention.

Other means for holding and positioning earphones 32a, 32b and ear housings 28a, 28b adjacent to a wearer's ears are also contemplated for use with the invention. As mentioned above, ear housings 28a, 28b may be attached directly to helmet 16 by VELCRO® type fasteners, snap fitting means or adhesives, and positioned such that earphones 32a, 32b are adjacent a wearer's ears and openings 30a, 30b are facing towards the rear. A thin, flexible strap which circumferentially encircles the wearer's head may be employed as an alternative to headband 38, with ear housings 28a, 28b and earphones 32a, 32b suitably positioned on the strap. It is additionally contemplated that, in situations wherein acoustic receiver 12 is coupled to a wearer's head by a hat or visor, ear housings 28a, 28b and earphones 32a, 32b could be coupled to the hat or visor in a manner which adequately positions ear housings 28a, 28b and earphones 32a, 32b adjacent to a wearer's ears.

Referring more particularly to FIG. 6, the present invention is preferably powered by a small replaceable battery 44 coupled to a circuit board 46 associated with acoustic receiver 12, with battery 44 interfaced with earphones 32a, 32b by wiring 34, and interfaced with microphone by wiring 48. Battery 44 would also power any associated amplifier circuitry included with the apparatus. A socket 50 is provided with circuit board 46 which engages jack 36 and thus provides for connection of earphones 32a, 32b with microphone 14 and battery 44. Battery 44 and circuit board 46 are shown as being internal to acoustic receiver 12, but may alternatively be external to acoustic receiver 12, and could be located within helmet 16 if desired. The power supply may alternatively comprise a solar cell array (not shown) on the top surface of helmet 16, with the solar cell array suitably interfaced with the circuitry. A volume control may also be included, particularly if an amplifier is used, to allow the user of the invention to increase or decrease the power output of earphones 32a, 32b as required. If desired, an FM radio, intercom system, or like audio system may be included with the invention in association with circuit board 46 to allow users of the invention to listen to radio broadcasts or to receive communication from others via speakers 32a, 32b.

The apparatus 10 is utilized by suitably affixing acoustic receiver 12 onto mounting elements 20a, 20b of helmet 16 by snap fitting pins 24a, 24b into slots 22a, 22b, such that the opening 52 of acoustic receiver 12 is facing in a rearward direction. Headband 38 is placed onto the wearer's head and ear housings 28a, 28b are positioned over the wearer's ears such that earphones 32a, 32b are adjacent to the wearer's ears and openings 30a, 30b face towards the rear. The user or wearer of the invention then places helmet 16 onto his or her head over headband 38 such that ear housings 28a, 28b are positioned adjacent notches 42a, 42b respectively.

Acoustic frequency vibrational waves, such as the sounds associated with an approaching motor vehicle or another bicyclist, are received by acoustic receiver 12 and reflected or otherwise directed towards microphone 14 by the parabolic-shaped interior of acoustic receiver 12. Microphone 14 produces an electric signal corresponding to the received sound which is transmitted via wiring 34, 48 to earphones 32a, 32b, wherein the sound received by acoustic receiver 12 is reproduced. Ear coverings 28a, 28b eliminate the ambient wind noise associated with cycle travel, so that the sounds produced by earphones 32a, 32b may be heard clearly by the user of the invention.

Use of the invention increases the safety of bicycle travel by allowing the wearer of the invention to hear sounds associated with vehicles approaching from behind which are not visible to the cyclist and would otherwise not be heard by the cyclist due to the ambient wind noise in the ears of the cyclist which is inherent in bicycle travel. The wearer of the invention, upon hearing a vehicle approaching from behind, may take responsive action, such as directing the bicycle towards the shoulder of the roadway, in order to avoid a collision. The invention may be utilized by cyclists in bicycle racing applications, as the invention allows the user to hear or detect the approach of other cyclists from behind without expending effort of turning the head to look for other cyclists.

While the invention is described herein in terms of use by bicyclists, it should be readily apparent that the invention may also be used by motorcyclists and by persons engaged in other non-cycling activities such as jogging wherein reception and amplification of sound from behind or outside the wearer's line of sight is desirable. While the invention is described in terms of utilizing rearward facing acoustic receiving means, the acoustic receiving means of the invention may be oriented in directions other than rearwardly disposed directions, such forwardly disposed or side-facing directions.

Accordingly, it will be seen that the present invention provides an acoustic receiver apparatus for use by cyclists which reduces or eliminates ambient wind noise due to air rushing past the cyclist's ears, and which receives sound from the rear direction and provides the sound to the wearer of the invention. Although the description above contains many specificities, these should not be construed as limiting the scope of the invention but as merely providing illustrations of some of the presently preferred embodiments of this invention. Thus, the scope of the invention should be determined by the appended claims and their legal equivalents.

What is claimed is:

1. Sound enhancing apparatus for wearing on a person's head and enhancing sounds received by a least one of said person's ears from a rearward direction relative to said person's head, comprising:

(a) a parabolic cup;

(b) a microphone positioned within said parabolic cup;

(c) an ear housing;

(d) an earphone electrically connected to said microphone, said earphone positioned within said ear housing;

(e) means, coupled to said parabolic cup, for supporting said parabolic cup on said person's head such that said parabolic cup receives sounds from a rearward direction relative to said person's head;

(f) means, coupled to said ear covering, for positioning and holding said speaker adjacent to a wearer's ear; and (g) means, coupled to said earphone, for supporting said earphone adjacent to said persons ear and within said ear housing.

2. An apparatus as recited in claim 1, further comprising power supply means for providing power to said microphone and said speaker.

3. A head worn acoustic receiver apparatus for enhancing sound received by a person's ears from a rearward direction relative to the person's head when said person is wearing a helmet, comprising:

(a) a parabolic cup;

(b) a microphone positioned within said parabolic cup;

(c) a first ear housing and a second ear housing;

(d) a first earphone and a second earphone, said first and second earphones electrically connected to said microphone;

(e) means, coupled to said parabolic cup, for coupling said parabolic cup to a helmet such that said parabolic cup receives sounds from a rearward direction relative to said person's head;

(f) means, coupled to said first and second ear housings, for supporting said first and second ear housings over said person's ears; and (g) means, coupled to said first and second earphones, for supporting said first and second earphones adjacent to said persons ears and within said first and second ear housings.

4. An apparatus as recited in claim 3, further comprising power supply means for providing power to said microphone and said earphones.

5. An apparatus as recited in claim 3, wherein said means for supporting said first and second earphones adjacent to said persons ears and within said first and second ear housings comprises a resilient hoop-shaped band, said band having a first end and a second end, said first earphone coupled to said first end of said band, said second earphone coupled to said second end of said band.

6. A helmet for enhancing sound received by a person's ears from a rearward direction relative to the person's head, comprising:

(a) a parabolic cup;

(b) a microphone, said microphone positioned within said cup;

(c) a first ear housing and a second ear housing;

(d) a first earphone and a second earphone, said first earphone included in said first ear housing, said second ear phone included in said second ear housing;

(e) a helmet, said helmet, having a front and a rear, said parabolic cup coupled to said rear of said helmet such that said parabolic cup receives sounds from a rearward direction relative to said person's head;

(f) means, coupled to said first and second ear housings, for supporting said first and second ear housings over said person's ears; and (g) means, coupled to said first and second earphones, for supporting said first and second earphones adjacent to said persons ears and within said first and second ear housings.

7. An apparatus as recited in claim 6, further comprising power supply means for providing power to said microphone and said earphones.

8. An apparatus as recited in claim 6, wherein said means for supporting said first and second ear housings over said person's ears and said means for supporting said first and second earphones adjacent to said persons ears and within said first and second ear housings comprises a resilient hoop-shaped band, said band having a first end and a second end, said first earphone and said first ear housing coupled to said first end of said band, said second earphone and said second ear housing coupled to said second end of said band.

9. An acoustic receiver apparatus as recited in claim 6, wherein said first and second ear housings each include a rearward facing opening.

* * * * *